United States Patent [19]
Digenis et al.

[11] Patent Number: 5,539,123
[45] Date of Patent: Jul. 23, 1996

[54] LOW MOLECULAR WEIGHT THIOCARBAMATES AS INHIBITORS OF ELASTASE, USES AND METHOD OF SYNTHESIS

[75] Inventors: George A. Digenis; Nikolaos P. Rodis, both of Lexington, Ky.

[73] Assignee: University of Kentucky Research Foundation, Lexington, Ky.

[21] Appl. No.: 296,623

[22] Filed: Aug. 26, 1994

[51] Int. Cl.$^6$ .......................... C07D 257/02; A61K 31/41
[52] U.S. Cl. ............................................................ 548/251
[58] Field of Search ............................ 548/251; 514/381

[56] References Cited

U.S. PATENT DOCUMENTS

| | | | |
|---|---|---|---|
| 4,643,991 | 2/1987 | Digenis et al. | 514/18 |
| 5,162,307 | 11/1992 | Digenis et al. | 514/19 |

OTHER PUBLICATIONS

Tuhy, et al., "Inhibition of Human Leukocyte Elastase by Peptide Chloromethyl Ketones" FEBS Letters, 50:359–61; 1975.

Powers, J. C. et al., "Specificity of Porcine Pancreatic Elastase, Human Leukocyte Elastase and Cathepsin G. Inhibition with Peptide Chloromethyl Ketones" Biochem. Biophys. Acta, 485:156–66; 1977.

Dorn, C. P., et al., "Proteinase Inhibitors. 1. Inhibitors of Elastase" J. Med. Chem., 20:1464–68; 1977.

Powers, J. C., et al., "Reaction of Serine Proteases with Aza–amino Acid and Aza–peptide Derivatives" Meth. Enzymol., 46:208–16; 1977.

Yoshimura, T., et al., "Specificity and Reactivity of Human Leukocyte Elastase, Porcine Pancreatic Elastase, Human Granulocyte Cathepsin G., and Bovine pancreatic Chymotrypsin with Arylsulfonyl Fluorides, Discovery of a new series of potent and specific irreversible Elastase Inhibitors" J. Biol. Chem., 257:5077–84; 1982.

Zimmerman, M., et al., "Inhibition of Elastase and Other Serine Proteases by Heterocyclic Acylating Agents" J. Biol. Chem., 25:9848–51; 1980.

Ashe, B. M. et al., "Selective Inhibition of Human Leukocyte Elastase and Bovine $a_1$–Chymotrypsin by Novel Heterocycles" J. Biol. Chem., 256:11603–6; 1981.

Groutas, W. C., et al., Biochem. Biophys. Res. Commun, 95:1980; 1980.

Scofield, R. E., et al., "p–Nitrophenyl Carbamates as Active–Site–Specific Reagents for Serine Proteases" Biochemistry, 16:2492; 1977.

Jaoff, A., et al., "Prevention of Elastase Induced Experimental Emphysema by Oral Administration of Synthetic Elastase inhibitor" Am. J. Respir. Dis., 121:1025–30; 1980.

Tsuji, K., et al., B.B.R.C., 122(2):571; 1984.

Digenis, G. A., et al., J. Med. Chem., 29:1468; 1986.

Gilman, A. G., et al., "The Pharmacological Basis of Therapeutics", MacMillan Publishing Co., p. 101; 1980.

Tarayre, J. P., et al., "Pharmacological studies in zymosan inflammation in rats and mice, I: Zymosan–induced paw edema in rat and mice" Pharmacological Res., 21(4):375–384; 1989.

Sato, T., et al., "Inhibitory effects of a novel synthetic protease inhibitor (FUT–175), on the paw edema in rats and Zymosan–induced compliment activation in vitro" Japan J. Pharmacol., 42:587–589; 1986.

Gremmell, D. K., et al., "Comparative effects of drugs on four paw edema models on the art" Agents and Actions, 9(1):107–116; 1979.

Keystone, D. C. et al., "Zyosan–induced arthritis: A model of chronic proliferative arthritis following activation of the alternative pathway of compliment" Arthritis and Rheumatism, 20(7): 1396–1401; 1977.

*Primary Examiner*—David B. Springer
*Attorney, Agent, or Firm*—Lowe, Price, LeBlanc & Becker

[57] ABSTRACT

A compound of the formula

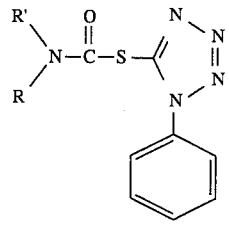

wherein R and R' together represent a primary or a secondary aliphatic amine. Also described are elastase enzyme inhibitory compositions including a carrier and an elastase enzyme inhibiting amount of the compounds of the invention. A method of selectively inhibiting the enzyme elastase in an animal or a human in need of such treatment includes administering to the animal or human an enzyme elastase inhibiting amount of one of the compounds of the invention or a composition thereof.

19 Claims, 5 Drawing Sheets

LOW MOLECULAR WEIGHT THIOCARBAMATES AS INHIBITORS OF ELASTASE, USES AND METHOD OF SYNTHESIS

TECHNICAL FIELD

This invention relates to potent low molecular weight thiocarbamate inhibitors of the enzyme elastase and to their utilization for inhibiting the activity of the enzyme in animals and humans. The invention also relates to a treatment of chronic tissue destruction in animals or humans, associated with a condition selected from the group consisting of inflammation, arthritis, emphysema, bronchitis, acute respiratory distress syndrome (ARDS), cystic fibrosis, and other conditions requiring elastase inhibition to reduce symptoms.

BACKGROUND

Proteinases from polymorphonuclear leukocytes and macrophages, especially elastases, for example human leukocyte elastase and cathepsin G, appear to be responsible for the chronic tissue destruction associated with inflammation, arthritis and emphysema. During infection or inflammation, the normal lung is protected from proteolytic digestion by the protease inhibitor, α1-antitrypsin. The protective mechanism appears to be nonoperative in individuals with an α1-antitrypsin deficiency due to genetic or other causes. Synthetic elastase inhibitors capable of replacing α1-antitrypsin may therefore be useful in the treatment of pulmonary emphysema and related diseases.

Several types of elastase inhibitors have been reported in the literature. These include peptide chloromethyl ketones as described by P. M. Tuhy and J. C. Powers, "Inhibition of Human Leukocyte Elastase by Peptide Chloromethyl Ketones", FEBS Letters, 50, 359–61 (1975); J. C. Powers, B. F. Gupton, A. D. Harley, N. Nishino and R. J. Whitley, "Specificity of Porcine Pancreatic Elastase, Human Leukocyte Elastase and Cathepsin G. Inhibition with Peptide Chloromethyl Ketones", Biochem. Biophys. Acta. 485, 156–66 (1977); azapeptides, C. P. Dorn, M. Zimmerman, S. S. Yang, E. C. Yurewicz, B. M. Ashe, R. Frankshun and H. Jones, "Proteinase Inhibitors. 1. Inhibitors of Elastase", J. med. Chem., 20, 1464–68 (1977); J. C. Powers and B. F. Gupton, "Reaction of Serine Proteases with Aza-amino Acid and Aza-peptide Derivatives", Meth. Enzymol., 46,208–16 (1977); sulfonyl fluorides, T. Yoshimura, L. N. Barker and J. C. Powers, "Specificity and. Reactivity of Human Leukocyte Elastase, Porcine Pancreatic Elastase, Human Granulocyte Cathepsin G, and Bovine Pancreatic Elastase, Human Granulocyte Cathepsin G, and Bovine pancreatic Chymotrypsin with Arylsulfonyl Fluorides. Discovery of a new series of potent and specific irreversible Elastase Inhibitors", J. Biol. Chem. 257, 5077–84 (1982); heterocyclic acylating agents, M. Zimmerman, H. Morman, D. Mulvey, H. Jones, R. Frankshum and B. M. Ashe, "Inhibition of Elastase and Other Serine Proteases by Heterocyclic Acylating Agents", J. Biol. Chem. 25, 9848–51 (1980); B. M. Ashe, R. L. Clark, H. Jones and M. Zimmerman, "Selective Inhibition of Human Leukocyte Elastase and Bovine $a_1$-Chymotrypsin by Novel Heterocycles", J. Biol. Chem. 256: 11603–6(1981); imidazole N-carboxamides, W. C. Groutas, R. C. Badger, T. D. Ocain, D. Felder, J. Frankson and M. Theodorakis, Biochem. Biophys. Res. Commun., 95, 1890 (1980); and p-nitrophenyl-N alkyl carbamates, R. E. Scofield, R. P. Werner and F. Wold, "p-Nitrophenyl Carbamates as Active-Site-Specific Reagents for Serine Proteases", Biochemistry, 16, 2492 (1977).

Some peptide chloromethyl ketones have been shown to be effective in preventing elastase induced emphysema in animal models, A. Jaoff and R. Dearing, "Prevention of Elastase Induced Experimental Emphysema by Oral Administration of Synthetic Elastase Inhibitor", Am. J. Respir. Dis. 121, 1025-3 (1980). However, there is considerable question whether such reactive agents can be used for treating emphysema in humans. This is not surprising since the alkylating moieties in these inhibitors might render them toxic when used on a continuous basis.

U.S. Pat. No. 4,643,991, Tsuji K. et al, B.B.R.C. 122(2):571 (1984) and Digenis, G. A. et al, J. Med. Chem. 29:1468 (1986) describe peptide elastase inhibitors which are specific and active-site directed.

Human Leucocyte Elastase (HLE) is a serine-dependent protease, which degrades elastin found in all elastic tissues. A growing body of experimental evidence indicates that this enzyme may be involved in tissue destruction associated with such disease states as arthritis, bronchitis, inflammation, acute respiratory distress syndrome (ARDS), cystic fibrosis, and pulmonary emphysema. In a healthy tissue a balance exists between elastase and the natural occurring antiprotease $a_1$-antitrypsin. Emphysema and other related diseases has been postulated to result from an imbalance between proteases such as HLE and their naturally occurring inhibitors (antiproteases) in the lung and other related tissues. Severe genetic deficiency in $a_1$-antitrypsin is frequently associated with development of pulmonary emphysema.

During the last 10 years potent oligopeptidyl carbamate esters like (PC1) (see formula 2) (U.S. Pat. No. 5,162,307) and (PC5) (see formula 2) (U.S. Pat. No. 4,643,991) have been shown to specifically inhibit HLE without inhibiting other similar enzymes in the body. The disadvantages of the oligopeptide inhibitors are first their multistep painstaking synthesis and purification which may render them expensive and difficult to manufacture, and second their questionable bioavailability especially oral due to their instability (chemical or enzymatic) in the G.I. tract.

To be suitable for human use, an enzyme inhibitor has to show a high degree of selectivity and must have minimal toxic side effects. As a result, most drugs are molecules that reversibly bind to specific enzymes or receptor sites. Examples are the carbamate esters physostigmine and neostigmine which have been clinically used as inhibitors of acetyl choline esterases (A. G. Gilman, L. S. Goodman, and A. Gilman, "The pharmacological Basis of Therapeutics", p. 101, MacMillan Publishing Co. (1980).

There is a need in the art for simple carbamate esters which are elastase inhibitors which have increased stability, activity and oral bioavailability.

The present invention overcomes the deficiencies of the prior art by providing for the design and synthesis of inhibitors of elastase which are simple carbamate esters with increased stability and oral bioavailability. The present invention elucidates the mechanism by which these carbamate esters inhibit elastase in vitro. The bioavailability and pharmacologic activity of the compounds of the invention, the most potent inhibitors of elastase, is shown in experimental animals in vivo. The compounds of the invention, unexpectedly and advantageously are more potent than known elastase inhibitors PC-1 and PC-5. In addition the compounds of the present invention unexpectedly and advantageously have increased absorption and bioavailability over the compounds PC-1 and PC-5.

DISCLOSURE OF THE INVENTION

The present invention is directed to a compound comprising a thiocarbamate including a primary or a secondary aliphatic amine and a 1-phenyl-1H-tetrazole-5-thiol. The present invention provides for a compound of the formula:

wherein R and R' together comprise a primary or a secondary aliphatic amine. Preferably the compound is a primary aliphatic amine, wherein R selected from the group consisting of $CH_3CH_2CH_2CH_2-$; $CH_2=CH-CH_2-$;

and a phenyl group and R' is H.

Alternatively, the compound of the invention is a secondary aliphatic amine, wherein R' is selected from the Group consisting of $CH_3CH_2CH_2CH_2-$;

and R is selected from $CH_3-CH_2$ and

The compound preferably is a compound which includes a primary or a secondary aliphatic amine and is selected from the group consisting of thiocarbamates N-butyl, 1-phenyl-1H-tetrazole-5-thiocarbamate; N-allyl, 1-phenyl-1H-tetrazole-5-thiocarbamate; N-isopropyl, 1-phenyl-1H-tetrazole-5-thiocarbamate; and N-phenyl, 1-phenyl-1H-tetrazole-5-thiocarbamate, N-Ethyl-N-n-butyl, 1-phenyl-1H-tetrazole-5-thiocarbamate, and N,N-diisopropyl, 1-phenyl-1H-tetrazole-5-thiocarbamate.

The compounds of the invention are useful in a method for the inhibition of elastase enzyme, particularly human leucocyte elastase, N-butyl, 1-phenyl-1H-tetrazole-5-thiocarbamate; N-allyl, 1-phenyl-1H-tetrazole-5-thiocarbamate; N-isopropyl, 1-phenyl-1H-tetrazole-5-thiocarbamate; and N-phenyl, 1-phenyl-1H-tetrazole-5-thiocarbamate.

An object of the invention is to provide a method for the inhibition of elastase enzyme wherein said patient has chronic tissue destruction associated with a condition selected from the group consisting of inflammation, arthritis, emphysema, bronchitis, acute respiratory distress syndrome (ARDS), and cystic fibrosis and other conditions requiring elastase inhibition to reduce symptoms.

Still another object of the invention is to provide for pharmaceutical compositions comprising the thiocarbamate compounds of the invention, including a primary or a secondary aliphatic amine and a 1-phenyl-1H-tetrazole-5-thiol, and a pharmaceutically acceptable carrier.

Preferably, the pharmaceutical composition includes a compound with a primary aliphatic amine which is selected from the group consisting of thiocarbamates N-butyl, 1-phenyl-1H-tetrazole-5-thiocarbamate; N-allyl, 1-phenyl-1H-tetrazole-5-thiocarbamate; N-isopropyl, 1-phenyl-1H-tetrazole-5-thiocarbamate; and N-phenyl, 1-phenyl-1H-tetrazole-5-thiocarbamate.

DESCRIPTION OF THE INVENTION

Human leucocyte elastase (HLE) is a serine dependent enzyme which in its active site utilizes the so-called "charged-relay system", a triad of amino acids -an aspartic acid, a histidine and a serine residue. A natural or a synthetic inhibitor should produce a tight binding with the active site which can lead to an increased rate of hydrolysis, producing inactive acylated enzyme. The rate of acylation and deacylation of the inactive acylated enzyme determine the extent of inhibition. Elastin, a component of connective tissue, is present in virtually every organ of the body and is the natural substrate of HLE. The polypeptide chain of elastin consists of elastic areas alternating with inelastic areas. The elastic areas are composed of largely hydrophobic (non-polar) amino acids such as glycine, alanine, proline and valine. The inelastic areas are composed of polyalanine sequences with interspersed lysine residues.

Based on the above, an effective inhibitor of elastase should meet the following requirements. It should be an ester that simulates the natural substrate elastin in incorporating aliphatic chains with similar hydrophobic character. Additionally it should be a good acylating agent so that it can form an acyl-enzyme complex in the serine residue of the active site with a low rate of deacylation.

The 1-phenyl-1H-tetrazole-5-thiol (D) (see scheme 1) is considered a good leaving group due to the thione-thiol tautomerization and this. should make the thiocarbamates good acylating reagents. The primary and secondary amine substituents with butyl, isopropyl, allyl, phenyl, ethyl-butyl, and diisopropyl were selected to test the requirement of HLE for a hydrophobic non polar residue in the substrate or inhibitor.

The designed and synthesized compounds, described herein, include, but are not limited to, thiocarbamates consisting of a primary or a secondary aliphatic amine and a 1-phenyl-1H-tetrazole-5-thiol. The primary thiocarbamates N-butyl, 1-phenyl-1H-tetrazole-5-thiocarbamate (1E), N-allyl, 1-phenyl-1H-tetrazole-5-thiocarbamate (2E), N-isopropyl, 1-phenyl-1H-tetrazole-5-thiocarbamate (3E), and N-phenyl, 1-phenyl-1H-tetrazole-5-thiocarbamate (4E) were synthesized according to scheme I below.

EXAMPLE 1

In the first reaction, the corresponding primary amine (A), (Scheme I) reacts with excess of carbonyl chloride (phosgene) (B) in toluene to produce the corresponding isocyanate (C) with concomitant release of hydrochloric acid. Then in the second reaction the isocyanate (C) reacts with excess of 1-phenyl-1H-tetrazole-5-thiol (D) in methylene chloride to produce the corresponding primary thiocarbamates (E).

The secondary thiocarbamates N-ethyl-N-butyl, 1-phenyl-1H-tetrazole-5-thiocarbamate (5E), and N, N-diisopropyl, 1-phenyl-1H-tetrazole-5-thiocarbamate (6E) were synthesized according to scheme II below.

EXAMPLE 2

In the first step the corresponding secondary amine (A), (Scheme II) reacts with excess of carbonyl chloride (phosgene) (B) in toluene resulting in the production of the corresponding carbamoyl chloride (C). In the second step the carbamoyl chloride (C) reacts with excess of 1-phenyl-1H-tetrazole-5-thiol (D) to produce the corresponding secondary thiocarbamates (E). Both scheme I and scheme II result in good yields of white crystalline products with the exception of (5SE) which is a yellowish oil.

SCHEME I

Synthesis of Primary Thiocarbamates
Scheme I

SCHEME I-continued

Synthesis of Primary Thiocarbamates
Scheme I

| | R— | F.W. | m.p. °C. | Yield % |
|---|---|---|---|---|
| (1) | $CH_3-CH_2-CH_2-CH_2-$ | 277.35 | 61–62 | 75–80 |
| (2) | $CH_2=CH-CH_2-$ | 261.30 | 92–93 | 75–80 |
| (3) | $\begin{array}{c} CH_3 \\ \phantom{CH_3}\diagdown \\ \phantom{CH_3}CH- \\ \phantom{CH_3}\diagup \\ CH_3 \end{array}$ | 263.32 | 89–90 | 70–75 |
| (4) | (phenyl) | 297.33 | 120–121 | 60–65 |

*in excess of the reagennt

SCHEME II

Synthesis of Secondary Thiocarbamates
Scheme II

SCHEME II-continued

Synthesis of Secondary Thiocarbamates
Scheme II b) 
R'—N(R)—C(Cl)=O + HS—[1-phenyl-1H-tetrazol-5-yl] (xs) →(Methylene chloride)→ R'—N(R)—C(=O)—S—[1-phenyl-1H-tetrazol-5-yl]

(C)  (D)   (E)

| | R | R' | F.W. | m.p. °C. | Yield % |
|---|---|---|---|---|---|
| (5) | CH₃—CH₂— | CH₃—CH₂—CH₂—CH₂ | 305.39 | Oil | 40–45 |
| (6) | (CH₃)₂CH— | (CH₃)₂CH— | 305.41 | 105–106 | 45–50 |

*in excess of the reagent

An alternative method scheme III has been proposed and tested for the synthesis of our compounds based on the synthesis of oligopeptidyl carbamate esters as HLE inhibitors from our labs.

EXAMPLE 3

According to scheme III in the first reaction 1-phenyl-1H-tetrazole-5-thiol (A) reacts with excess of carbonyl chloride (phosgene) (B) in toluene to produce 1-phenyl-1H-tetrazole-5-thiochloroformate (C) with simultaneous release of hydrochloric acid. In the second reaction the 1-phenyl-1H-tetrazole-5-thiochloroformate (C) reacts with the primary or secondary thiocarbamates (E).

In practice scheme III has a disadvantage over scheme I and II. The crude product from the second reaction of scheme III is a reaction mixture which after recrystallization yields 80% of the urea (F) of the corresponding amine. Purification of the rest of the reaction mixture by silica gel flash chromatography, results in poor yields of the desired thiocarbamate never exceeding 15–20%. This indicates that the major product of scheme III is the corresponding urea (F) and as a result the method was less preferred.

EXAMPLE 4

Stability of N-n-Butyl,
1-Phenyl-1H-Tetrazole-5-Thiocarbamate (1E) in
Excess of Methanol with Normal Phase HPLC

A separation between (1E) and (D) was achieved in normal phase chromatography conditions with a PARTISIL-50 normal phase silica column and 0.05% acetic acid in methylene chloride mobile phase. The flow was maintained at 1 ml/min, and a KRATOS variable UV detector at 265 nm was used. Two separate experiments were conducted under the above conditions in which the stability of (1E) was

SCHEME III

Alternative Synthesis of Thiocarbamates

-continued
SCHEME III

CH₃—CH₂—CH₂—CH₂—NH—C(=O)—NH—CH₂—CH₂—CH₂—CH₃

(F) main product

*in excess of the reagent monitored in excess of methanol. In the first experiment the disappearance of (1E) was monitored with time in excess of methanol and from the slope of the logarithmic curve of the concentration of (1E) vs. time the pseudofirst order rate constant is determined at $1.65 \times 10^{-3}$ hr$^{-1}$.

In the second experiment again the disappearance of the thiocarbamate (1E) is measured by monitoring now the appearance of 1-phenyl-1H-tetrazole-5-thiol (D) with time and from the slope of the logarithmic curve vs time we determine the pseudofirst order rate constant which is $1.71 \times 10^{-3}$ hr$^{-1}$.

The above two experiments indicate that (1E) is consumed at the same rate as the thiol tetrazole (D) is produced. The thiol tetrazole (D) is exclusively produced from the degradation of the thiocarbamate with methanol. In other words (1E) reacts with methanol to give thiol tetrazole (D) and most probably N-n-butyl, methylcarbamate which cannot be detected under the above conditions. The half life as calculated from the pseudofirst order rate constants is 17 days indicating that (1E) is a fairly stable compound in excess of methanol.

EXAMPLE 5

Inactivation of Human Leucocyte Elastase by the Primary and Secondary Thiocarbamates The novel compounds synthesized (1E–6E, Formula 1), were evaluated for their ability to inhibit the HLE-catalyzed hydrolysis of N-Methoxysuccinyl-L-Ala-L-Ala-L-Pro-L-Val-p-nitroanilide and were found to exhibit time dependent inhibition of this enzyme. Therefore, second order rate constants ($k_{obs}/I$, $M^{-1}$ $s^{-1}$), (I=concentration inhibitor molar) shown in Formula 1, were determined by following the inactivation of the enzyme for 2 hours as

FORMULA 1
Inhibition of Thiocarbamate compounds against HLE

| | R | R' | $k_{obs}/I$ ($M^{-1}$ $s^{-1}$) |
|---|---|---|---|
| (1) | CH₃—CH₂—CH₂—CH₂— | H— | $2.1 \times 10^5$ |
| (2) | CH₂=CH—CH₂— | H— | $6.1 \times 10^4$ |
| (3) | (CH₃)₂CH— | H— | $3.3 \times 10^3$ |
| (4) | phenyl | H— | $1.9 \times 10^2$ |
| (5) | CH₃—CH₂— | CH₃—CH₂—CH₂—CH₂— | $1.8 \times 10^2$ |
| (6) | (CH₃)₂CH— | (CH₃)₂CH— | N.I.* |

*No inhibitory activity described in the experimental section. Generally, the compounds always in excess are incubated for different time intervals with the enzyme and at the end of the incubation interval the substrate is added and the absolute remaining activity of the enzyme is measured as described in the enzymatic assay of the experimental section. The results are plotted as % of relative remaining activity vs time which is the absolute remaining activity in the presence of inhibitor divided by the absolute remaining activity of the free enzyme in absence of inhibitor for the same time interval.

All of the studied inhibitors except the phenyl thiocarbamate (5E) show initially a pseudofirst order rate profile which ends in zero order at longer times. The phenyl thiocarbamate (5E) shows only pseudofirst order rate profile. The enzyme appears to react with the inhibitor in a pseudofirst order manner to produce a modified enzyme which is partially active and maintains a fractional activity (F) compared to the original activity. In such a case a semilog plot of the relative remaining activity (A/Ao) vs time would describe a curve approaching the fractional activity (F) at longer times whereas a semilog plot of (A/Ao-F)/(1-F) vs time will be linear with a slope equal to the $k_{obs}$, the pseudofirst order rate constant (equation 2).

The inactivation of HLE enzyme appears to involve the chemical modification of one residue on the enzyme and the pseudofirst order rate constant $k_{obs}$ divided by the concentration of the inhibitor (I) can be used as a measure of the inhibitory activity of the compounds (equation 3). It follows that the larger the number of $K_{obs}/I$ (Ksec) the greater the inhibiting capacity of the compound.

Thus, compound N-n-butyl, 1-phenyl-1H-tetrazole-5-thiocarbamate (1E) exhibits the highest inhibitory activity ($k_{obs}/I=2.1\times10^5$ $M^{-1}s^{-1}$) indicating the trend that straight chain nonpolar aliphatic substituents are essential for high activity. Indeed the N-allyl, 1-phenyl-1H-tetrazole-5-thiocarbamate (2E) with the polar straight chain due to the double bond has the second highest inhibitory activity of all thiocarbamates ($k_{obs}/I=6.1\times10^4$ $M^{-1}s^{-1}$).

Furthermore the most polar aromatic N-phenyl, 1-phenyl-1H-tetrazole-5-thiocarbamate (4E) is one of the least active thiocarbamates ($k_{obs}/I=1.9\times10^2$ $M^{-1}s^{-1}$) with activity similar to the N-ethyl-N-butyl, 1-phenyl-1H-tetrazole-5-thiocarbamate (5E) ($k_{obs}/I=1.8\times10^2$ $M^{-1}s^{-1}$). The N-isopropyl, 1-phenyl-1H-tetrazole-5-thiocarbamate (3E) ($k_{obs}/I=3.3\times10^3$ $M^{-1}s^{-1}$) is 10 times more active than (4E) and N, N-diisopropyl, 1-phenyl-1H-tetrazole-5-thiocarbamate (6E) has no inhibitory activity against HLE.

The fact that secondary thiocarbamates have the least or no activity along with the low activity of (3E) indicates a second important trend, the degree of branching of the side chain. The inhibitory activity decreases as the degree of branching on the side chain increases. None of the corresponding amines (1A, 2A, 3A, 4A, 5A and 6A) nor 1-phenyl-1H-tetrazole-5-thiol (D) inhibited HLE.

When compared to the oligopeptidyl carbamate specific inhibitor of HLE (PC1), synthesized previously in our labs, with $k_{obs}/I=3.3\times10^4$ $M^{-1}s^{-1}$ only N-n-butyl, 1-phenyl-1H-tetrazole-5-thiocarbamate (1E), and N-allyl, 1-phenyl-1H-tetrazole-5-thiocarbamate (4E) were found 10 and 2 times more potent, respectively. Formula 2 shows the structure of comparative compound PC-1 and PC-5.

Finally the low molecular weight thiocarbamates provide an advantage over their oligopeptidyl predecessors firstly due to their simple one or two step synthesis, secondly due to their improved or comparable

FORMULA 2 activity and lastly due to their potential increased oral bioavailability.

EXAMPLE 6

Synthesis of Primary and Secondary Thiocarbamates

Proton NMR spectra were recorded on a Varian VXR-300 NMR spectrometer with tetramethylsilane as internal standard (δ scale) in $CDCl_3$. Elemental analyses were conducted by the Atlantic Microlab, Inc., Atlanta, Ga. and the results were within 0.4% of the theoretical values.

I.R. spectra were determined in KBr discs, as Nujol mulls or liquid films on a Perkin Elmer 567 spectrophotometer. Melting points were determined on a Fisher-Hohns Unimelt apparatus and are uncorrected. Reactions were routinely followed by thin layer chromatography (TLC) using Whatman K67 silica gel plates, and spots were visualized either by UV irradiation at 254 mn or by iodine chamber.

Compounds (1E), (3E), and (6E) were recrystallized from 2-propanol and water, (4E) was recrystallized from acetone and water, (2E) was recrystallized from isopropyl ether, and finally flash chromatograpy for the purification of (5E) was performed with Alumina gel.

Ir and NMR spectra were consistent with the assigned structures of all new compounds and intermediates. The reported yields were generally the result of a single experiment and were not optimized.

EXAMPLE 7

Method A: Synthesis of Primary Thiocarbamates

N-n-Butyl, 1-Phenyl-1H-tetrazole-5-thiocarbamate (1E). (Scheme I)

a) Synthesis of n-butylisocyanate (1C).

A solution of n-butylamine (1A) 3.7 g in 50 ml toluene was added in an excess of 33.7 ml carbonyl chloride solution (phosgene) (Fluka Chemicals) (B) solution 20% in toluene over a period of 1 hour at below $-15°$ C. and it was left at room temperature stirring overnight. The excess of carbonyl chloride was removed by a stream of dry air, and the precipitated n-butylamine hydrochloride was filtered and washed with chloroform. The combined filtrate and washings were then distilled under vacuum and the distillates were characterized by IR. The distillate with the largest characteristic peak at 2360 $cm^{-1}$ was the n-butylisocyanate (1C) and it was used as is to the next step.

b) Synthesis of N-n-butyl, 1-phenyl-1H-tetrazole-5-hiocarbamate (1E).

1.63 ml n-butylisocyanate (1C) from the previous step or purchased commercially (Aldrich Chemicals) was added over a period of 1 hour in an excess of a 1-phenyl-1H-tetrazole-5-thiol (D) (Aldrich Chemicals) solution 3.1 g in 120 ml methylene chloride stirring at room temperature and it was left to react overnight. The reaction then was concentrated in a rotary evaporator and triturated with hexane to give a crude white solid which was reconcentrated three times more with hexane. The crude solid was slurred in md 2-propanol and heated at reflux until it was in solution. After filtering the hot solution the filtrate was cooled in an ice bath for 20 min and water was added until permanent cloudiness appeared. Then it was reheated at reflux until it was again in solution.

The solution was allowed to cool to 20°–25° C. for 12 hours and aged another 12 hours at 0°–5° C. The precipitated white crystalline solid was filtered and dried to afford 3.1 g (80% yield) of (1E), mp 61°–62° C., proton NMR: 1.0 (t,3H), 1.48 (sext., 2H), 1.69 (p, 2H), 3.57 (q, 2H), 7.6–7.77 (m, 5H), 9.7 (s, 1H), $^{13}$C NMR: 12.8, 20.0, 31, 40.8, 124.6, 129.8, 130.5, 134, 146, 162.3. Elemental analysis found ($C_{12}H_{15}N_5OS$) C: 51.88, H: 5.45, N: 25.25, S: 11.57.

The following compounds were synthesized by analogous procedures: N-allyl, 1-phenyl-1H-tetrazole-5-thiocarbamate (2E) white crystalline solid from the reaction of allylisocyanate (2C) (Aldrich Chemicals) with 1-phenyl-1H-tetrazole-5-thiol (D), was recrystallized from isopropyl ether, yield 80%, mp 92°–93° C., $^1$H NMR: 3.8 (q, 2H), 5.1 (d, 1HO, 5.3 (d, 1H), 5.9 (m, 1H), 7.4–7.7 (m, 5H). Elemental analysis ($C_{11}H_{11}N_5OS$) C: 50.55, H: 4.22, N: 26.89, S: 12.25.

N-isopropyl, 1-phenyl-1H-tetrazole-5-thiocarbamate (3E) white crystalline solid from the reaction of isopropylisocyanate (3F) (IR: 2260 $cm^{-1}$), prepared as described above from phosgene and isopropyl amine, or purchased commercially (Aldrich Chemicals), and 1-phenyl-1H-tetrazole-5-thiol (D) was recrystailized from isopropyl alcohol and water, yield 75%, mp 89°–90° C., $^1$H NMR 1.5 (d, 6H), 3.48 (m, 1H), 7.6–7.8 (m, 5H). Elemental analysis ($C_{11}H_{13}N_5OS$) C: 50.16, H: 4.97, N: 26 . 65, S: 12.23.

N-phenyl, 1-phenyl-1H-tetrazole-5-thiocarbamate (4E) white crystalline solid from the reaction of phenylisocyanate (4C) (Aldrich Chemicals) and 1-phenyl-1H-tetrazole-5-thiol (D), was recrystallized from acetone water, yield 63%, mp 120°–121° C., $^1$H NMR: 7.4–8.0 (m, 10H). Elemental analysis ($C_{14}H_{11}N_5OS$) C: 56.47, H: 3.7, N: 23.5, S: 10.26.

EXAMPLE 8

Method B: Synthesis of Secondary Thiocarbamates

N-Ethyl-N-n-butyl,1-phenyl-1H-tetrazole-5-thiocarbamate (5E). (Scheme II)

a) Synthesis of Ethyl, n-butyl carbamoyl chloride (5C).

4.5 ml ethyl, butylamine were added in an excess of 18 ml carbonyl chloride (phosgene) (Fluka Chemicals) (B) solution 20% in toluene over a period of 1 hour at below $-15°$ C. and it was left at room temperature to react overnight. The excess of carbonyl chloride was removed by a stream of dry air and the precipitated ethyl, butylamine hydrochloride was filtered and washed with chloroform. The filtrate and the washings were then distilled under vacuum and the distillates were characterized by IR, $^1$H NMR and $^{13}$C NMR. The distillate with the following characteristics was (5C) and it was used without any further purification to the next step. IR: strong carbonyl peak at 1738 $cm^{-1}$, and strong aliphatic peak at 2950 $cm^{-1}$. $^1$H NMR: 0.96 (t, 3H), 1.22 (t, 3H), 1.34 (m, 2H), 1.61 (m, 2H), 3.39 (m, 4H). $^{13}$C NMR: 12.7, 13.7, 19.9, 30, 45.5, 50, 148.8.

b) Synthesis of N-Ethyl-N-n-butyl, 1-phenyl-1H-tetrazole-5-thiocarbamate (5E).

5.4 ml ethyl, n-butyl carbamoyl chloride (5C) from the previous step was added over a period of half hour in an excess of 1-phenyl-1H-tetrazole-5-thiol (D) (Aldrich Chemicals) solution 7.13 g in 240 ml methylene chloride stirring at room temperature and it was left to react overnight. The reaction mixture was then concentrated in a rotary evaporator to give 5 g of an oily residue. The product was purified by alumina gel flash chromatography with 5% methanol in methylene chloride and the fractions collected were monitored by TLC in UVat 254 nmto afford 4.2 g, 42% yield of the oily product N-ethyl-N-n-butyl, 1-phenyl-1H-tetrazole-5-thiocarbamate (5E) after evaporation of the solvent. $^1$H NMR: 0.8–1.6 (m, 10H), 3.3 (m, 4H), 7.56 (m, 5H). $^{13}$C NMR: 12.7, 13.7, 19.8, 30.5, 43.5, 48, 125.1, 128.3, 129.3, 130.5, 134, 147, 159. Elemental analysis ($C_{14}H_{19}N_5OS$) C: 55.05, H: 6.34, N: 22.99, S: 10.57.

In a similar manner the following compound was synthesized:

N,N-diisopropyl 1-phenyl-1H-tetrazole-5-thiocarbamate (6E) is a white crystalline solid produced from the reaction of diisopropyl carbamoyl chloride (6C) (Aldrich Chemicals) and 1-phenyl-1H-tetrazole-5-thiol (D), was recrystallized from a mixture of isopropyl alcohol and water or a mixture of dimethyl formamide and water, yield 47%, $^1$H NMR: 1.2 (d, 12H), 3.4 (m, 1H), 3.85 (m, 1H), 7.45–7.6 (m, 5H). Elemental analysis ($C_{14}H_{19}N_5OS$) C: 55.05, H: 6.30, N: 22.91, S: 10.42.

EXAMPLE 9

Method C: Alternative Synthesis of Thiocarbamates

N-n-butyl, 1-phenyl-1H-tetrazole-5-thiocarbamate (5E) (Scheme III).

a) Synthesis of 1-Phenyl-1H-tetrazole-5-thiochloroformate (C).

A solution of 4 g 1-phenyl-1H-tetrazole-5-thiol (A) in 90 ml tetrahydrofurane was added in an excess of 15.5 ml carbonyl chloride solution (phosgene) (Fluka Chemicals)

(B) 20% toluene, over a period of half hour at below −20° C. and it was left at room temperature stirring overnight. The excess of carbonyl chloride was removed with a stream of dried air and the solvent was evaporated in a rotary evaporator. The solid residue was recrystallized from ethylacetate and hexane. The crude solid was heated at reflux with ethylacetate until it was all dissolved and after warm filtering it was cooled in an ice bath. Then hexane was added until permanent turbidity was formed and was reheated at reflux until it was again in solution.

The solution was allowed to cool and age at room temperature over a period of 2 hours and at 0°–5° C. for another 4 hours. The precipitated crystalline solid was filtered and dried to afford 3.2 g of 1-phenyl-1H-tetrazole-5-thiochloroformate (C) (57% yield), mp 121°–122° C., IR: 1715 $cm^{-1}$ carbonyl, 3060 $cm^{-1}$ aromaticity, $^{13}$C NMR: 125, 130, 131.5, 133, 144, 176.5, $^1$H NMR: 7.4 (m, 2H), 7.6 (m, 3H).

b) Synthesis of N-n-butyl, 1-phenyl-1H-tetrazole-5-thiocarbamate (5E).

0.93 ml n-butyl amine (5D) (Aldrich Chemicals) in 20 ml methylene chloride was added in an excess of 2.5 g 1-phenyl-1H-tetrazole-5-thiochloroformate (C) solution in 120 ml methylene chloride over a period of half hour and it was left stirring at room temperature to react overnight. The reaction mixture was concentrated in a rotary evaporator and triturated with petroleum ether resulting in crude yellowish solid after evaporation of the solvent. The crude solid was recrystallized by a mixture of acetone and water with a procedure similar to that described in the previous step to afford 0.98 g of a white crystalline product, mp 70°–71° C., which was identified to be N,N'-di-n-butyl, urea (5F) and not the desired product (5E). Yield 80% IR: 1620 cm-1 carbonyl (upfield characteristic for ureas), 3140 and 3325 cm-1N-H stretching vibration. 1H NMR: 0.93 (t, 3H), 1.35 (m, 2H), 1.48 (m, 2H), 3.15 (m, 2H), 4.22 (s, 1H).

In a second attempt of the same reaction after discarding the triturated from petroleum ether solid urea (5F) the filtrate was introduced into a silica gel flash chromatography column and washed with chloroform. Fractions were collected and detected by TLC in UV at 254 nm. The fractions corresponding to (5E) were collected and characterized as described at method A to give 39 mg of (5E) 15% yield. Method C was less preferred.

EXAMPLE 10

Enzyme Inhibition Kinetics

Human leucocyte elastase from human sputum was purchased from elastin corporation. Hepes, 4-(2-hydroxyethyl)-1-piperazineethanesulfonic acid, was purchased from Aldrich Chemical Co. (Milwaukee, Wis.). Substrate N-Methoxysuccinyl-L-Ala-L-Ala-L-Pro-L-Val-p-nitroanilide was purchased from Sigma Chemicals. Absorbance was measured with a VARIAN CARY-2200 spectrophotometer at 410 nm.

a) Enzyme Assay.

2.9 ml Hepes buffer (0.1M Hepes, 0.05M NaCL, 10% Dimethyl Sulfoxide, adjusted with 6N NaOH at ph=7.5), 50 µl of inhibitor solution always in excess of enzyme in Dimethyl sulfoxide, are placed in each of two 3 ml quartz cuvettes. 5 µl of acetate buffer (0.05M Sodium Acetate adjusted with 6N HCl to ph=5.5) is added to the reference cuvette, and the cuvette is shaken for 15 seconds to mix the solution. 5 µl of HLE $3.7 \times 10^{-5}$M in acetate buffer is added to the sample cuvette and the cuvette is shaken for 15 seconds. Both cuvettes were placed in the jacketed cuvette holders of the spectrophotometer and incubated at 25° C. for a fixed time interval up to 2 hours (Incubation periods of 3, 4, 5, 7, 10, 15, 20, 30, 45, 60, 90 and 120 minutes were used).

Shortly before the incubation period ends, the cuvettes are balanced at 410 nm. 50 µl of HLE substrate $2.8 \times 10^{-2}$M in Dimethyl sulfoxide is added to both the reference and sample cuvette, with addition to the sample cuvette marking the end of the incubation time. The cuvettes are shaken for 15 seconds and the absorbance is recorded at 410 nm at 1 min, 2 min and 3 min after addition of substrate. A control in which 50 µl of dimethyl sulfoxide used to dissolve the inhibitor is added in its place, is done in the same manner as above for each incubation period.

The final Dimethyl sulfoxide concentration never exceeded 12% v/v. Absorbance of sample is the absolute remaining activity of HLE (A), and absorbance of control is the total activity of HLE (Ao).

% Relative Remaining Activity=(A/Ao)×100

The % relative remaining activity of the HLE for each inhibitor is plotted against the time of incubation and from the slope of the semilog plot the $k_{obs}$ is determined.

b) Modelling the inhibition.
Enzyme kinetics.

The enzyme (E) reacts with the excess of inhibitor (I) in a pseudofirst order rate process to produce the modified enzyme (E') which is partially active and has fractional activity F compared to the original activity Ao.

The equation that describes this model is:

$$A/Ao=(1-F)e^{-Kobst}+F \qquad \text{(equation 1)}$$

Rearranging results in a linear relationship $$Ln\,((A/Ao)-F/1-F)=-k_{obs}t \qquad \text{(equation 2)}$$

A semilog plot results in a straight line with slope=$k_{obs}$, the pseudofirst order rate constant $$k_{sec}=k_{obs}/I \qquad \text{(equation 3)}$$

The $k_{sec}$ is the second order independent rate constant that is used to compare the inhibitory activity of the compounds against HLE.

Summary of Results with Compound PC-16

Attached are results which show strong evidence of the ability of an exemplary compound of the present invention, compound PC-16, to act as an antiarthritic drug in the Zymosan-induced arthritis, an acceptable animal model of chronic proliferative arthritis in the rat. The rat is an acceptable experimental animal model for correlation to human utility, and the present results constitute excellent proof for the value of the compounds of the present invention as elastase inhibitors.

Compound PC-16

Protocol of Arthritic Study

A reversible arthritic condition was induced according to known procedures for the Zymosan-induced arthritis (See J. P. Tarayre, A. Delphon, et al., Pharmacological studies in zymosan inflammation in rats and mice, I: Zymosan-induced paw edema in rat and mice, Pharmacological Research, 21, (#4) 375–384 (1989); Takuo Sato, Yoshitaka Ino, et al., Inhibitory effects of a novel synthetic protease inhibitor (FUT-175), on the paw edema in rats and Zymosan-induced compliment activation in vitro, Japan J. Pharmacol., 42, 587–589 (1986); David K. Gremmell, et al., Comparative effects of drugs on four paw edema models on the rat, Agents and Actions 4, (#1) 107–116 (1979); and D. C. Keystone, et al., Zymosan-induced arthritis: A model of chronic proliferative arthritis following activation of the alternative pathway of compliment, Arthritis and Rheumatism 20 (#7) 1396–1401 (1977)).

Each rat (250 g each) was kept in a restraining cage with light ether anesthesia until the administration of the drug. The procedure involves the intramuscular (IM) injection of 1 mg of Zymosan in 50 μL (microliters) of normal saline in the pad of a hind paw of the rat. Swelling becomes evident within 20 minutes and reaches a maximum within 1.5 hours. The swelling disappears after 24 hours. In the Figures the reversal to normal size of the paw within 24 hours is not shown. The degree of swelling is measured by a water displacement method and the percent (%) of volume increase of the paw is plotted against time (see J. P. Tarayre, A. Delphon, et al., Pharmacological studies in zymosan inflammation in rats and mice. I: Zymosan-induced paw edema in rat and mice, Pharmaco-logical Research, 21, (#4) 375–384 (1989); Takuo Sato, Yoshitaka Ino, et al., Inhibitory effects of a novel synthetic protease inhibitor (FUT-175), on the paw edema in rats and Zymosan-induced compliment activation in vitro, Japan J. Pharmacol., 42, 587–589 (1986)).

Figure 1:
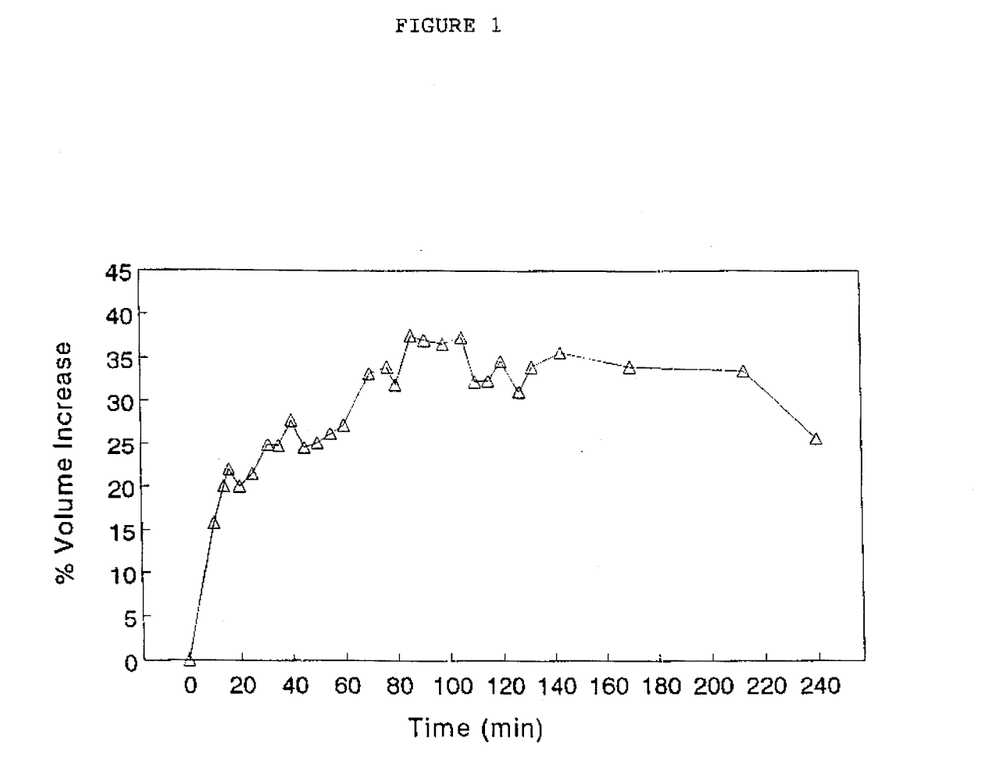
FIGS. 1 show the percent volume increase of the paw after IM (intramuscular injection) of Zymosan (1 mg/50 µl normal saline per paw) only.
Figure 1A:
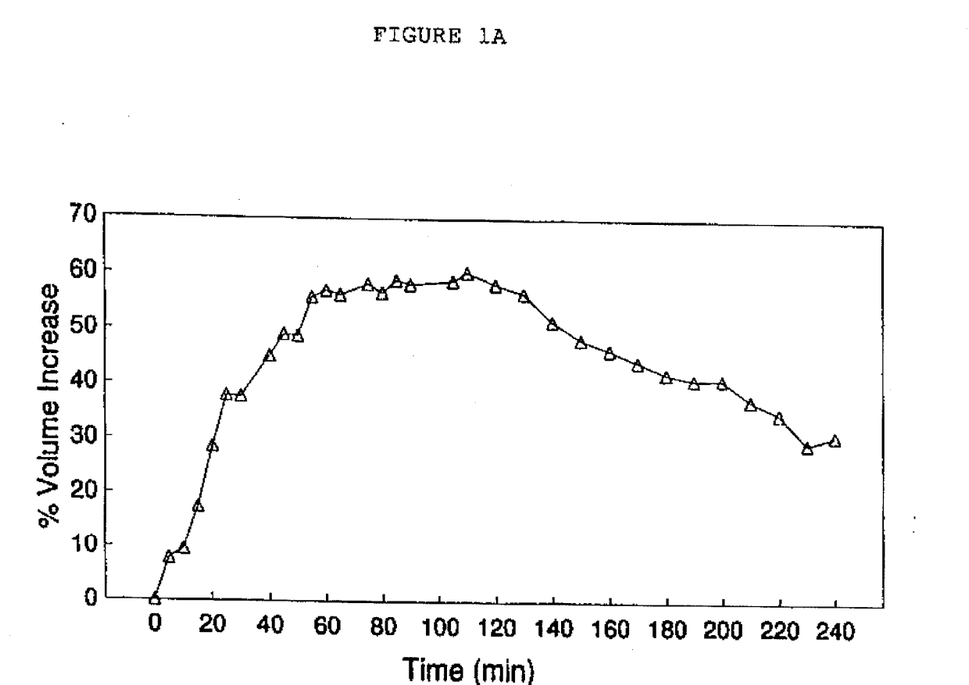
FIG. 1a shows that the percent (%) of volume increase of the paw of control animals which received IP (intraperitoneally) 100 µl of propylene glycol (the vehicle of the drug) 15 minutes prior to Zymosan administration.

FIG. 1 shows the percent (%) of volume increase of the paw after I.M. injection of Zymosan (1 mg/paw in 50 μl normal saline). Control was conducted by injecting I.P. 100 μl of propylene glycol (the vehicle) 15 min. prior to Zymosan administration. FIG. 1a shows the percent (%) of volume increase of the paw in control animals with time which reaches a value of 60% within 1.5h. Data from tables 1 and 1a are plotted in FIGS. 1 and 1a respectively.

TABLE 1

| | Zymosan Inflammation in Rats | | | | | | | |
|---|---|---|---|---|---|---|---|---|
| | Experiment #1 | | Experiment #2 | | Experiment #3 | | | |
| Time (min) | Volume (ml) | % Volume Increase | Volume (ml) | % Volume Increase | Volume (ml) | % Volume Increase | Mean of 3 experiments | Standard Deviation |
| 0   | 1.53 | 0.0  | 1.53 | 0.0  | 1.65 | 0.0  | 0.00  | 0.00 |
| 10  | 1.74 | 13.7 | 1.74 | 13.7 | 1.98 | 20.0 | 15.82 | 3.62 |
| 14  | 1.83 | 19.6 | 1.83 | 19.6 | 2.00 | 21.0 | 20.07 | 0.80 |
| 16  | 1.86 | 21.6 | 1.86 | 21.6 | 2.03 | 23.0 | 22.05 | 0.83 |
| 20  | 1.78 | 16.3 | 1.83 | 19.6 | 2.05 | 24.0 | 19.98 | 3.84 |
| 25  | 1.84 | 20.3 | 1.84 | 20.3 | 2.05 | 24.0 | 21.51 | 2.16 |
| 31  | 1.91 | 24.8 | 1.91 | 24.8 | 2.06 | 25.0 | 24.89 | 0.09 |
| 35  | 1.90 | 24.2 | 1.90 | 24.2 | 2.08 | 26.0 | 24.79 | 1.05 |
| 40  | 1.96 | 28.1 | 1.96 | 28.1 | 2.10 | 27.0 | 27.74 | 0.64 |
| 45  | 1.81 | 18.3 | 1.95 | 27.5 | 2.11 | 28.0 | 24.58 | 5.45 |
| 50  | 1.83 | 19.6 | 1.94 | 26.8 | 2.13 | 29.0 | 25.14 | 4.91 |
| 55  | 1.89 | 23.5 | 1.93 | 26.1 | 2.13 | 29.0 | 26.22 | 2.74 |
| 60  | 1.90 | 24.2 | 1.95 | 27.5 | 2.15 | 30.0 | 27.21 | 2.92 |
| 70  | 2.04 | 33.3 | 2.04 | 33.3 | 2.19 | 33.0 | 33.22 | 0.19 |
| 77  | 2.05 | 34.0 | 2.05 | 34.0 | 2.21 | 34.0 | 33.99 | 0.01 |
| 80  | 1.98 | 29.4 | 2.01 | 31.4 | 2.23 | 35.0 | 31.93 | 2.84 |
| 86  | 2.11 | 37.9 | 2.11 | 37.9 | 2.26 | 37.0 | 37.61 | 0.52 |
| 91  | 2.09 | 36.6 | 2.09 | 36.6 | 2.28 | 38.0 | 37.07 | 0.81 |
| 98  | 2.08 | 35.9 | 2.08 | 35.9 | 2.28 | 38.0 | 36.63 | 1.18 |
| 105 | 2.09 | 36.6 | 2.09 | 36.6 | 2.29 | 39.0 | 37.40 | 1.38 |
| 110 | 1.89 | 23.5 | 2.07 | 35.3 | 2.28 | 38.0 | 32.27 | 7.69 |
| 115 | 1.92 | 25.5 | 2.06 | 34.6 | 2.26 | 37.0 | 32.38 | 6.08 |
| 120 | 2.05 | 34.0 | 2.05 | 34.0 | 2.24 | 36.0 | 34.66 | 1.16 |
| 127 | 1.92 | 25.5 | 2.03 | 32.7 | 2.23 | 35.0 | 31.06 | 4.96 |
| 132 | 2.05 | 34.0 | 2.05 | 34.0 | 2.21 | 34.0 | 33.99 | 0.01 |
| 143 | 2.08 | 35.9 | 2.08 | 35.9 | 2.23 | 35.0 | 35.63 | 0.55 |
| 170 | 2.05 | 34.0 | 2.05 | 34.0 | 2.21 | 34.0 | 33.99 | 0.01 |
| 213 | 2.10 | 37.3 | 2.01 | 31.4 | 2.18 | 32.0 | 33.54 | 3.23 |
| 240 | 1.92 | 25.5 | 1.92 | 25.5 | 2.08 | 26.0 | 25.66 | 0.29 |

TABLE 1a

Zymosan Induced Inflammation in Rats
Control Experiment with solvent (0.1 ml Propylene Glycol)

| Time (min) | Experiment #1 Volume (ml) | Experiment #1 % Volume Increase | Experiment #2 Volume (ml) | Experiment #2 % Volume Increase | Experiment #3 Volume (ml) | Experiment #3 % Volume Increase | Mean of 3 experiments | Standard Deviation |
|---|---|---|---|---|---|---|---|---|
| 0 | 1.67 | 0.00 | 1.80 | 0.00 | 1.85 | 0.00 | 0.00 | 0.00 |
| 5 | 1.80 | 7.78 | 1.94 | 8.00 | 1.99 | 7.67 | 7.82 | 0.17 |
| 10 | 1.83 | 9.60 | 1.97 | 9.45 | 2.03 | 9.54 | 9.53 | 0.08 |
| 15 | 1.96 | 17.4 | 2.12 | 17.9 | 2.17 | 17.1 | 17.5 | 0.41 |
| 20 | 2.15 | 28.7 | 2.30 | 27.6 | 2.39 | 29.1 | 28.5 | 0.78 |
| 25 | 2.30 | 37.7 | 2.49 | 38.2 | 2.55 | 37.8 | 37.9 | 0.26 |
| 30 | 2.22 | 32.9 | 2.51 | 39.6 | 2.60 | 40.5 | 37.7 | 4.13 |
| 40 | 2.42 | 44.9 | 2.62 | 45.3 | 2.68 | 45.1 | 45.1 | 0.19 |
| 45 | 2.49 | 49.1 | 2.67 | 48.6 | 2.77 | 49.5 | 49.1 | 0.45 |
| 50 | 2.48 | 48.5 | 2.68 | 49.1 | 2.75 | 48.8 | 48.8 | 0.30 |
| 55 | 2.62 | 56.9 | 2.80 | 55.4 | 2.87 | 55.3 | 55.9 | 0.89 |
| 60 | 2.62 | 56.9 | 2.82 | 56.7 | 2.91 | 57.5 | 57.0 | 0.42 |
| 65 | 2.56 | 53.3 | 2.83 | 57.4 | 2.92 | 58.1 | 56.3 | 2.60 |
| 75 | 2.64 | 58.1 | 2.85 | 58.5 | 2.92 | 58.1 | 58.2 | 0.24 |
| 80 | 2.51 | 50.3 | 2.87 | 59.6 | 2.96 | 60.2 | 56.7 | 5.55 |
| 85 | 2.65 | 58.7 | 2.87 | 59.3 | 2.94 | 58.8 | 58.9 | 0.33 |
| 90 | 2.63 | 57.5 | 2.86 | 58.9 | 2.93 | 58.2 | 58.2 | 0.71 |
| 105 | 2.67 | 59.9 | 2.86 | 58.8 | 2.92 | 57.8 | 58.8 | 1.04 |
| 110 | 2.71 | 62.3 | 2.87 | 59.3 | 2.95 | 59.6 | 60.4 | 1.64 |
| 120 | 2.65 | 58.7 | 2.85 | 58.5 | 2.92 | 57.6 | 58.3 | 0.58 |
| 130 | 2.61 | 56.3 | 2.83 | 57.1 | 2.90 | 56.6 | 56.7 | 0.41 |
| 140 | 2.54 | 52.1 | 2.73 | 51.5 | 2.80 | 51.4 | 51.7 | 0.38 |
| 150 | 2.48 | 48.5 | 2.67 | 48.6 | 2.74 | 47.9 | 48.3 | 0.38 |
| 160 | 2.45 | 46.7 | 2.65 | 47.0 | 2.70 | 45.8 | 46.5 | 0.63 |
| 170 | 2.41 | 44.3 | 2.60 | 44.4 | 2.67 | 44.5 | 44.4 | 0.09 |
| 180 | 2.36 | 41.3 | 2.56 | 42.3 | 2.65 | 43.0 | 42.2 | 0.85 |
| 190 | 2.36 | 41.3 | 2.55 | 41.5 | 2.60 | 40.5 | 41.1 | 0.53 |
| 200 | 2.42 | 44.9 | 2.51 | 39.7 | 2.57 | 38.8 | 41.1 | 3.30 |
| 210 | 2.30 | 37.7 | 2.47 | 37.2 | 2.54 | 37.1 | 37.3 | 0.34 |
| 220 | 2.25 | 34.7 | 2.43 | 35.0 | 2.50 | 35.3 | 35.0 | 0.28 |
| 230 | 2.18 | 30.5 | 2.33 | 29.4 | 2.38 | 28.7 | 29.5 | 0.93 |
| 240 | 2.21 | 32.3 | 2.35 | 30.5 | 2.41 | 30.2 | 31.0 | 1.16 |

In the experimental procedure the drug [PC-16, 9 g/rat (FIG. 2) or 90 μg/rat (FIG. 3)] is dissolved in 100 μL of propylene glycol and is injected IP to the rats. Fifteen minutes later the Zymosan (1mg/50 μL of normal saline) solution is injected IM into the paw of the rats. The degree of swelling is subsequently measured at various time intervals for a period of 24 hours and is reported up to 4 hours.

DETAILED DESCRIPTION OF THE FIGURES

FIGS. 1 and 1a show that the percent (%) of volume increase of the paw of the rats reaches a value of 60% within 1.5 hours.

Figure 2:
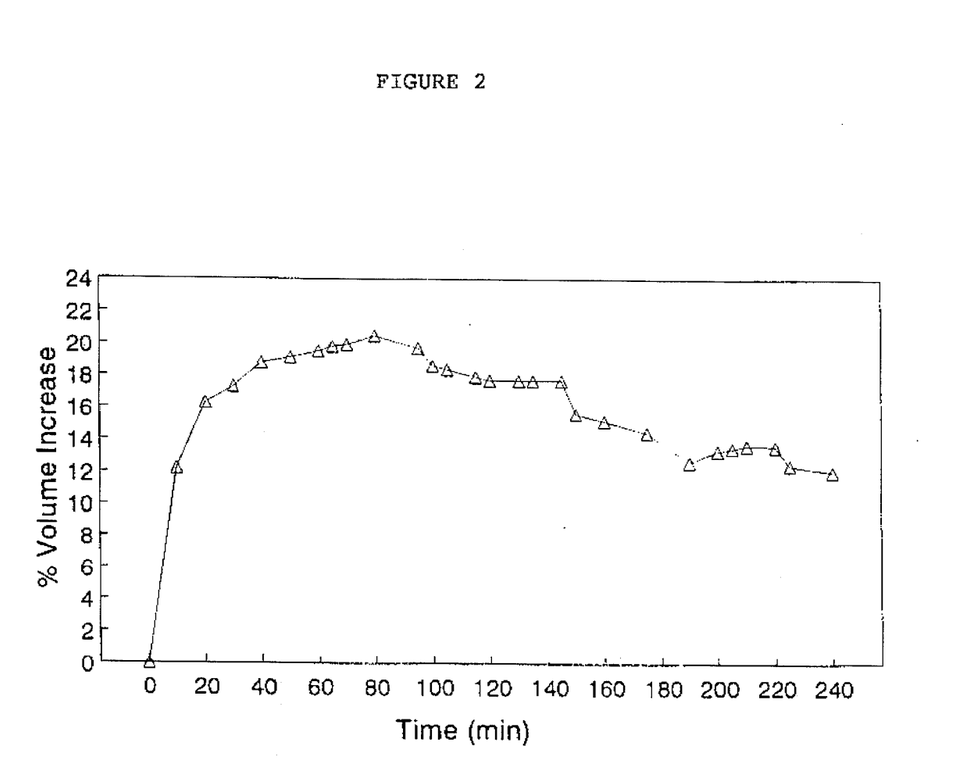
FIG. 2 shows the percentage volume increase of rat paw with time after IP administration of PC-16. ($3.6\times10^{-5}$ mg/g of rat body weight which translates to a dose of 36 µg/kg of rat body weight PC-16) 15 min prior to IM in injection of Zymosan (1 mg/50 µl normal saline per paw). There is only a 20% maximum swelling at the 1.5 hour mark.

When 36 μg/kg of compound PC-16 (FIG. 2, shows $3.6 \times 10^{-5}$ mg/g of rat body weight which translates to a dose of 36 μg/kg) is injected IP to rats the percent (%) volume increase is only 20% at the 1.5 hour mark. This means that the swelling was reduced from 60% to 20% with 36 μg/kg of compound PC-16. (see FIG. 2 which plots data of Table 2 below).

TABLE 2

Zymosan Induced Inflammation in Rats
Treatment with PC16 ($3.6 \times 10^{-5}$ mg/g of Rat Body Weight)

| Time (min) | Experiment #1 Volume (ml) | Experiment #1 % Volume Increase | Experiment #2 Volume (ml) | Experiment #2 % Volume Increase | Experiment #3 Volume (ml) | Experiment #3 % Volume Increase | Mean of 3 experiments | Standard Deviation |
|---|---|---|---|---|---|---|---|---|
| 0 | 1.94 | 0.00 | 1.89 | 0.00 | 1.65 | 0.00 | 0.00 | 0.00 |
| 10 | 2.17 | 11.9 | 2.14 | 13.2 | 1.84 | 11.5 | 12.2 | 0.91 |
| 20 | 2.26 | 16.5 | 2.18 | 15.3 | 1.93 | 17.1 | 16.3 | 0.89 |
| 30 | 2.29 | 18.0 | 2.20 | 16.4 | 1.94 | 17.5 | 17.3 | 0.84 |
| 40 | 2.30 | 18.6 | 2.24 | 18.5 | 1.97 | 19.3 | 18.8 | 0.44 |
| 50 | 2.31 | 19.1 | 2.26 | 19.6 | 1.96 | 18.8 | 19.1 | 0.39 |
| 60 | 2.32 | 19.6 | 2.26 | 19.6 | 1.97 | 19.4 | 19.5 | 0.11 |
| 65 | 2.33 | 20.1 | 2.26 | 19.6 | 1.98 | 19.8 | 19.8 | 0.26 |
| 70 | 2.33 | 20.1 | 2.25 | 19.0 | 1.99 | 20.7 | 20.0 | 0.84 |

TABLE 2-continued

Zymosan Induced Inflammation in Rats
Treatment with PC16 ($3.6 \times 10^{-5}$ mg/g of Rat Body Weight)

| Time (min) | Experiment #1 | | Experiment #2 | | Experiment #3 | | Mean of 3 experiments | Standard Deviation |
|---|---|---|---|---|---|---|---|---|
| | Volume (ml) | % Volume Increase | Volume (ml) | % Volume Increase | Volume (ml) | % Volume Increase | | |
| 80  | 2.30 | 18.6 | 2.31 | 22.2 | 1.99 | 20.7 | 20.5 | 1.84 |
| 95  | 2.29 | 18.0 | 2.30 | 21.7 | 1.97 | 19.4 | 19.7 | 1.85 |
| 100 | 2.29 | 18.0 | 2.23 | 18.0 | 1.98 | 19.8 | 18.6 | 1.03 |
| 105 | 2.30 | 18.6 | 2.23 | 18.0 | 1.96 | 18.6 | 18.4 | 0.34 |
| 115 | 2.29 | 18.0 | 2.22 | 17.5 | 1.95 | 18.3 | 17.9 | 0.43 |
| 120 | 2.30 | 18.6 | 2.21 | 16.9 | 1.94 | 17.6 | 17.7 | 0.82 |
| 130 | 2.28 | 17.5 | 2.23 | 18.0 | 1.94 | 17.6 | 17.7 | 0.25 |
| 135 | 2.28 | 17.5 | 2.23 | 18.0 | 1.94 | 17.6 | 17.7 | 0.25 |
| 145 | 2.30 | 18.6 | 2.22 | 17.5 | 1.93 | 17.1 | 17.7 | 0.76 |
| 150 | 2.26 | 16.5 | 2.17 | 14.8 | 1.91 | 15.5 | 15.6 | 0.84 |
| 160 | 2.23 | 14.9 | 2.18 | 15.3 | 1.90 | 15.2 | 15.2 | 0.20 |
| 175 | 2.23 | 14.9 | 2.17 | 14.8 | 1.87 | 13.5 | 14.4 | 0.80 |
| 190 | 2.16 | 11.3 | 2.16 | 14.3 | 1.85 | 12.3 | 12.6 | 1.50 |
| 200 | 2.22 | 14.4 | 2.14 | 13.2 | 1.85 | 12.3 | 13.3 | 1.07 |
| 205 | 2.16 | 11.3 | 2.21 | 16.9 | 1.85 | 12.2 | 13.5 | 3.01 |
| 210 | 2.21 | 13.9 | 2.17 | 14.8 | 1.85 | 12.2 | 13.6 | 1.33 |
| 220 | 2.20 | 13.4 | 2.16 | 14.3 | 1.87 | 13.1 | 13.6 | 0.62 |
| 225 | 2.19 | 12.9 | 2.12 | 12.2 | 1.85 | 12.2 | 12.4 | 0.41 |
| 240 | 2.17 | 11.9 | 2.13 | 12.7 | 1.84 | 11.6 | 12.1 | 0.57 |

Figure 3:
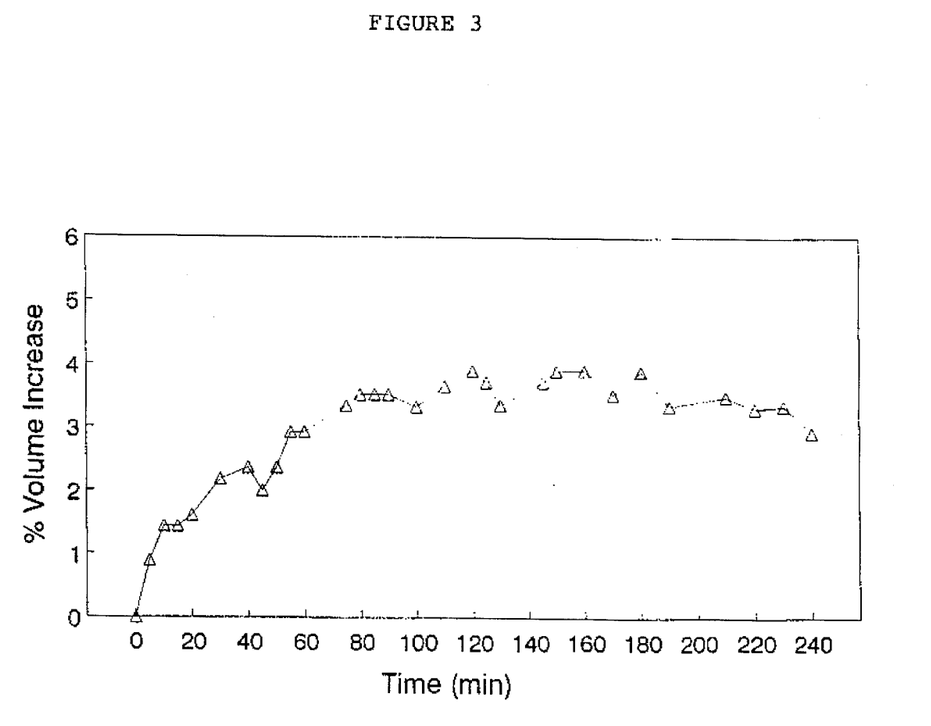
FIG. 3 shows the percent volume increase of rat paw with time after IP injection of PC-16 (at a dose of 360 µg/kg of rat body weight PC-16) 15 min prior to IM in injection of Zymosan (1 mg/50 µl normal saline per paw). There is practically no swelling.

At a dose of 360 μg/kg of compound PC-16 there is practically no swelling (see FIG. 3 which plots data of Table 3 below).

TABLE 3

Zymosan Induced Inflammation in Rats
Treatment with PC16 ($3.6 \times 10^{-4}$ mg/g of Rat Body Weight)

| Time (min) | Experiment #1 | | Experiment #2 | | Experiment #3 | | Mean of 3 experiments | Standard Deviation |
|---|---|---|---|---|---|---|---|---|
| | Volume (ml) | % Volume Increase | Volume (ml) | % Volume Increase | Volume (ml) | % Volume Increase | | |
| 0   | 1.80 | 0.00 | 1.85 | 0.00 | 1.65 | 0.00 | 0.00 | 0.00 |
| 5   | 1.82 | 1.11 | 1.86 | 0.54 | 1.67 | 1.02 | 0.89 | 0.31 |
| 10  | 1.83 | 1.67 | 1.87 | 1.08 | 1.68 | 1.55 | 1.43 | 0.31 |
| 15  | 1.83 | 1.67 | 1.87 | 1.08 | 1.68 | 1.55 | 1.43 | 0.31 |
| 20  | 1.83 | 1.67 | 1.88 | 1.62 | 1.68 | 1.55 | 1.61 | 0.06 |
| 30  | 1.84 | 2.22 | 1.89 | 2.16 | 1.69 | 2.18 | 2.19 | 0.03 |
| 40  | 1.84 | 2.22 | 1.90 | 2.70 | 1.69 | 2.18 | 2.37 | 0.29 |
| 45  | 1.81 | 0.56 | 1.90 | 2.70 | 1.70 | 2.75 | 2.00 | 1.25 |
| 50  | 1.83 | 1.67 | 1.90 | 2.70 | 1.70 | 2.75 | 2.37 | 0.61 |
| 55  | 1.85 | 2.78 | 1.91 | 3.24 | 1.70 | 2.75 | 2.92 | 0.28 |
| 60  | 1.85 | 2.78 | 1.91 | 3.24 | 1.70 | 2.75 | 2.92 | 0.28 |
| 75  | 1.86 | 3.33 | 1.91 | 3.24 | 1.71 | 3.44 | 3.34 | 0.10 |
| 80  | 1.86 | 3.33 | 1.92 | 3.78 | 1.71 | 3.44 | 3.52 | 0.24 |
| 85  | 1.86 | 3.33 | 1.92 | 3.78 | 1.71 | 3.44 | 3.52 | 0.24 |
| 90  | 1.86 | 3.33 | 1.92 | 3.78 | 1.71 | 3.44 | 3.52 | 0.24 |
| 100 | 1.84 | 2.22 | 1.93 | 4.32 | 1.71 | 3.44 | 3.33 | 1.06 |
| 110 | 1.86 | 3.33 | 1.94 | 4.86 | 1.70 | 2.75 | 3.65 | 1.09 |
| 120 | 1.86 | 3.33 | 1.94 | 4.86 | 1.71 | 3.50 | 3.90 | 0.84 |
| 125 | 1.85 | 2.78 | 1.94 | 4.86 | 1.71 | 3.50 | 3.71 | 1.06 |
| 130 | 1.84 | 2.22 | 1.93 | 4.32 | 1.71 | 3.50 | 3.35 | 1.06 |
| 145 | 1.85 | 2.78 | 1.94 | 4.86 | 1.71 | 3.50 | 3.71 | 1.06 |
| 150 | 1.86 | 3.33 | 1.94 | 4.86 | 1.71 | 3.50 | 3.90 | 0.84 |
| 160 | 1.86 | 3.33 | 1.94 | 4.86 | 1.71 | 3.50 | 3.90 | 0.84 |
| 170 | 1.86 | 3.33 | 1.92 | 3.78 | 1.71 | 3.44 | 3.52 | 0.24 |
| 180 | 1.87 | 3.89 | 1.93 | 4.32 | 1.71 | 3.44 | 3.88 | 0.44 |
| 190 | 1.86 | 3.33 | 1.91 | 3.24 | 1.71 | 3.44 | 3.34 | 0.10 |
| 210 | 1.88 | 4.44 | 1.91 | 3.24 | 1.70 | 2.75 | 3.48 | 0.87 |
| 220 | 1.88 | 4.44 | 1.90 | 2.70 | 1.70 | 2.75 | 3.30 | 0.99 |
| 230 | 1.87 | 3.89 | 1.90 | 2.70 | 1.71 | 3.44 | 3.34 | 0.60 |
| 240 | 1.86 | 3.33 | 1.90 | 2.70 | 1.70 | 2.75 | 2.93 | 0.35 |

Figure 4:
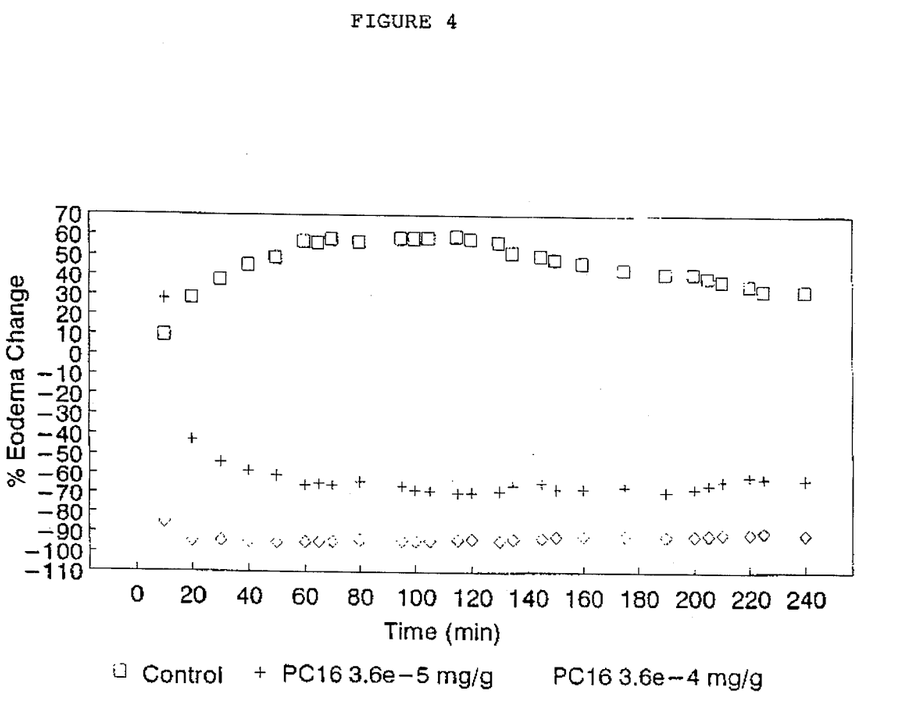
FIG. 4 shows the impressive oedema reduction of rat paw treated with PC-16 prior to the Zymosan injection compared with control.

FIG. 4 shows the impressive reduction in edema swelling when compound PC-16 is injected prior to the Zymosan injection. FIG. 4 plots data of Table 4 below).

TABLE 4

Zymosan Induced Inflammation in Rats

| Time (min) | Control (0.1 ml prop. glyc.) | Treatment with PC16 ($3.6 \times 10^{-5}$ mg/g b.w.) | | Treatment with PC16 ($3.6 \times 10^{-4}$ mg/g b.w.) | |
|---|---|---|---|---|---|
| | | % Volume Increase | % Oedema Volume change | % Volume Increase | % Oedema Volume change |
| 10 | 9.53 | 12.2 | 28.0 | 1.43 | −85.0 |
| 20 | 28.5 | 16.3 | −42.8 | 1.61 | −94.4 |
| 30 | 37.7 | 17.3 | −54.1 | 2.19 | −94.2 |
| 40 | 45.1 | 18.8 | −58.3 | 2.37 | −94.7 |
| 50 | 48.8 | 19.1 | −60.8 | 2.37 | −95.1 |
| 60 | 57.0 | 19.5 | −65.8 | 2.92 | −94.9 |
| 65 | 56.3 | 19.8 | −64.8 | 2.92 | −94.8 |
| 70 | 58.2 | 20.0 | −65.7 | 3.13 | −94.6 |
| 80 | 56.7 | 20.5 | −63.9 | 3.52 | −93.8 |
| 95 | 58.6 | 19.7 | −66.4 | 3.52 | −94.0 |
| 100 | 58.5 | 18.6 | −68.2 | 3.33 | −94.3 |
| 105 | 58.8 | 18.4 | −68.7 | 3.49 | −94.1 |
| 115 | 59.6 | 17.9 | −69.9 | 3.78 | −93.7 |
| 120 | 58.3 | 17.7 | −69.6 | 3.90 | −93.3 |
| 130 | 56.7 | 17.7 | −68.8 | 3.35 | −94.1 |
| 135 | 51.7 | 17.7 | −65.8 | 3.53 | −93.2 |
| 145 | 50.0 | 17.7 | −64.6 | 3.71 | −92.6 |
| 150 | 48.3 | 15.6 | −67.7 | 3.90 | −91.9 |
| 160 | 46.5 | 15.2 | −67.4 | 3.90 | −91.6 |
| 175 | 43.3 | 14.4 | −66.7 | 3.70 | −91.5 |
| 190 | 41.1 | 12.6 | −69.2 | 3.34 | −91.9 |
| 200 | 41.1 | 13.3 | −67.6 | 3.41 | −91.7 |
| 205 | 39.2 | 13.5 | −65.6 | 3.41 | −91.3 |
| 210 | 37.3 | 13.6 | −63.4 | 3.48 | −90.7 |
| 220 | 35.0 | 13.6 | −61.2 | 3.30 | −90.6 |
| 225 | 32.6 | 12.4 | −61.9 | 3.32 | −89.8 |
| 240 | 32.3 | 12.1 | −62.7 | 2.93 | −90.9 |

As pointed out above, the compounds of the invention may be employed as specific active site directed inhibitors of the enzyme, elastase. For this purpose, the compounds are preferably combined with a pharmaceutically acceptable carrier for administration by injection or in the oral form. Conventional adjuvant and carriers may be employed in combination with about 0.001 to 2.0 weight percent of the active compound.

Conventional adjuvants and methods of administration are known in the art as set forth in Remington's Pharmaceutical Sciences, 18th ed., Mack Publishing Co., 1992, incorporated herein by reference in its entirety. The compounds may be administered to animals or humans at a range between 36 and 360 μg/kg.

In sum, the present invention provides for a compound of the formula wherein R and R' together comprise a primary or a secondary aliphatic amine. Preferably the compounds is a primary aliphatic amine, wherein R selected from the group consisting of $CH_3CH_2-$; $CH_2=CH-CH_2-$;

and a phenyl group and R' is H.

Alternatively, the compound of the invention is a secondary aliphatic amine, wherein R' is selected from the Group consisting of $CH_3CH_2CH_2CH_2-$;

and R is selected from $CH_3-CH_2$ and

The purpose of the above description and examples is to illustrate some embodiments of the present invention without implying any limitation. It will be apparent to those of skill in the art that various modifications and variations may be made to the composition and method of the present invention without departing from the spirit or scope of the invention. All publications and patents mentioned herein are incorporated by reference in their entireties.

We claim:

1. A compound of the formula wherein R and R' are selected from the group consisting of alkyl, alkenyl and phenyl amines; and wherein said compound is a primary or secondary amine.

2. A compound according to claim 1 which is a primary amine, wherein R selected from the group consisting of $CH_3CH_2CH_2CH_2—$; $CH_2=CH—CH_2—$;

and a phenyl group and R' is H.

3. A compound according to claim 1, which is a secondary amine, wherein R' is selected from the Group consisting of $CH_3CH_2CH_2CH_2—$;

and R is selected from $CH_3—CH_2$ and

4. The compound of claim 1, wherein said compound includes a primary amine and said compound is selected from the group consisting of N-(n-butyl) 1-phenyl-1H-tetrazole-5-thiocarbamate; N-allyl 1-phenyl-1H-tetrazole-5-thiocarbamate; N-isopropyl 1-phenyl 1H-tetrazole-5-thiocarbamate; and N-pheny 1-phenyl-1H-tetrazole-5-thiocarbamate.

5. The compound of claim 1, wherein said compound is a secondary amine selected from the group consisting of N-Ethyl, N-n-(Butyl) 1-phenyl-1H-tetrazole-5-thiocarbamate, and N,N-diisopropyl 1-phenyl-1H-tetrazole-5-thiocarbamate.

6. A method of selectively inhibiting the enzyme elastase in an animal or a human in need of such treatment comprising administering to said animal or human an enzyme elastase inhibiting amount of the compound of claim 1.

7. A pharmaceutical composition comprising a compound of the formula wherein R and R' are selected from the group consisting of alkyl, alkenyl and phenyl amines, and wherein said compound is a primary or secondary amine; and a pharmaceutically acceptable carrier.

8. A pharmaceutical composition according to claim 7, wherein said compound is a primary amine, wherein R selected from the group consisting of $CH_3CH_2CH_2CH_2—$; $CH_2=CH—CH_2—$;

and a phenyl group and R' is H.

9. A pharmaceutical composition according to claim 7, wherein said compound is a secondary amine, wherein R' is selected from the group consisting of $CH_3CH_2CH_2CH_2—$;

and R is selected from $CH_3—CH_2$ and

10. The composition of claim 8, wherein said compound includes a primary amine and is selected from the group consisting of N-(n-butyl) 1-phenyl-1H tetrazole-5-thiocarbamate; N-allyl 1-phenyl-1H-tetrazole-5-thiocarbamate; N-isopropyl 1-phenyl-1H-tetrazole-5-thiocarbamate; and N-phenyl 1-phenyl-1H-tetrazole-5-thiocarbamate.

11. The composition of claim 7 wherein said compound includes a secondary amine and is selected from the group consisting of N-Ethyl, N-(n-Butyl) 1-phenyl-1H-tetrazole-5-thiocarbamate and N,N-diisopropyl 1-phenyl-1H-tetrazole-5-thiocarbamate.

12. A method for the synthesis of the primary thiocarbamates of claim 10 as human leucocyte elastase (HLE) inhibitors, comprising the steps of:

(a) reacting a primary amine with excess of carbonyl chloride in toluene resulting in tile production of the corresponding isocyanate; and, (b) reacting the isocyanate with excess of 1-phenyl-1H-tetrazole-5 -thiol to produce the corresponding primary thiocarbamate.

13. A method for the synthesis of the secondary thiocarbamates of claim 11 human leukocyte elastase (HLE) inhibitors, comprising the steps of:

(a) reacting a secondary amine with excess of carbonyl chloride in toluene resulting in the production of the corresponding carbamoyl chloride; and, (b) reacting the carbamoyl chloride with excess of 1-phenyl-1H-tetrazole-5-thiol to produce the corresponding secondary thiocarbamates.

14. The method of claim 6, wherein said human or animal has chronic tissue destruction associated with arthritis.

15. The method of claim 6, wherein said human or animal has chronic tissue destruction associated with emphysema.

16. The method of claim 6, wherein said human or animal has chronic tissue destruction associated with bronchitis.

17. The method of claim 6, wherein said human or animal has chronic tissue destruction associated with acute respiratory distress syndrome (ARDS).

18. The method of claim 6, wherein said human or animal has chronic tissue destruction associated with cystic fibrosis.

19. The method of claim 6, wherein said human or animal has chronic tissue destruction associated with inflammation.

* * * * *